US00PP12560P2

(12) United States Plant Patent
Ullrich

(10) Patent No.: US PP12,560 P2
(45) Date of Patent: Apr. 23, 2002

(54) CHRYSANTHEMUM PLANT NAMED 'DARK CANTATA'

(75) Inventor: Peter F. Ullrich, Coral Gables, FL (US)

(73) Assignee: Flores Esmeralda Ltda., LaCaja-Autioquia (CO)

( * ) Notice: Subject to any disclaimer, the term of this patent is extended or adjusted under 35 U.S.C. 154(b) by 0 days.

(21) Appl. No.: 09/664,132

(22) Filed: Sep. 19, 2000

(51) Int. Cl.[7] ..... A01H 5/00
(52) U.S. Cl. ..... Plt./297

(58) Field of Search ..... Plt./297

*Primary Examiner*—Bruce A. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Dark Cantata', characterized by its daisy-type inflorescenses that are about 6.8 cm in diameter; lavender-colored ray florets; uniform flowering habit; early flowering; dark green foliage; strong flowering stems; and good postproduction longevity with inflorescences maintaining good substance and color for more than two weeks in an interior environment.

2 Drawing Sheets

BACKGROUND OF THE INVENTION

The present invention relates to a new and distinct cultivar of Chrysanthemum plant, botanically known as *Dendranthema grandiflora* and referred to by the cultivar name Dark Cantata.

The new Chrysanthemum was discovered by the Inventor in a controlled environment La Ceja-Antioquia, Colombia as a naturally-occurring whole plant mutation of the Chrysanthemum cultivar Cantata., disclosed in U.S. Plant Pat. No. 8,172. The selection of this plant was based on its lavender-colored ray florets compared to the light pink-colored ray florets of plants of the cultivar Cantata.

Asexual reproduction of the new Chrysanthemum by terminal cuttings taken in a controlled environment in La Ceja-Antioquia, Colombia, has shown that the unique features of this new Chrysanthemum are stable and reproduced true to type in successive generations.

SUMMARY OF THE INVENTION

The cultivar Dark Cantata has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dark Cantata'. These characteristics in combination distinguish 'Dark Cantata'as a new and distinct cultivar:

1. Large daisy-type inflorescences that are about 6.8 cm in diameter.

2. Lavender-colored ray florets.

3. Uniform flowering habit.

4. Early flowering, response time is about 53 days.

5. Dark green foliage.

6. Strong flowering stems.

7. Good postproduction longevity with inflorescences maintaining good substance and color for more than two weeks in an interior environment.

BRIEF DESCRIPTION OF THE PHOTOGRAPHS

The accompanying colored photographs illustate the overall appearance of the new Chrysantemum, showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the first sheet comprises a side perspective view of a typical flowering stem of 'Dark Cantata' grown as a spray-type cut Chrysanthemum.

The photograph at the bottom of the first sheet comprises a close-up view of typical inflorescences of 'Dark Cantana'.

The photograph at the top of the second sheet is a close-up view of the upper and lower surfaces of typical inflorescences of 'Dark Cantata'.

The photograph in the middle of the second sheet comprises a close-up view of typical inflorescences of 'Dark Cantata' (left) and 'Cantata' (right).

The photograph at the bottom of the second sheet comprises a close-up view of typical inflorescences of 'Dark Cantata' (left) and 'Cantata' (right).

DETAILED BOTANICAL DESCRIPTION

The following observations and measurements describe plants that were grown in La Ceja-Antioquia, Columbia, under conditions which approximate commercial practice in a single-layer polyethylene-covered greenhouse. Rooted cuttings were planted in November, 1999, and received 17 long day/short nights followed by short day/long nights until flowering. Plants were grown as single-stem cut chrysanthemums. During the production time, the following environmental conditions were measured: day temperatures averaged 20° C.; night temperatures averaged 11.5° C.; and light level was about 3,500 foot-candles. Measurements and numerical values represent averages for six typical flowering stems. Color references are made to The Royal Horticultural Society Colour Chart except where general terms of ordinary dictionary significance are used.

Botanical classification: *Dendranthema grandiflora* cultivar Dark Cantata.

Commercial classification: Daisy spray-type cut Chrysanthemum.

Parentage: Naturally-occurring whole plant mutation of *Dendranthema grandiflora* cultivar Cantata, disclosed in U.S. Plant Pat. No. 8,172.

Propagation:

*Type.*—Terminal tip cuttings.

*Time to produce a rooted cutting.*—Summer: About 10 to 11 days with temperatures at 23° C. Winter: About 11 to 12 days with temperatures at 16° C.

*Root description.*—Fine, fibrous and well-branched.

Plant description:

*Appearance.*—Herbaceous daisy spray-type cut flower. Stems upright, uniform habit and freely branching.

*Flowering stem length.*—About 90 cm.

*Stem color.*—146A.

*Foliage description.*—Arrangement: Alternate. Length: About 6.8 cm. Width: About 3.9 cm. Apex: Mucronate. Base: Attenuate. Margin: Palmately lobed; sinuses mostly divergent. Texture: Upper and lower surfaces slightly pubescent. Veins prominent on lower surface. Color: Young and mature foliage, upper surface: 147A. Young and mature foliage, lower surface: Close to 147B. Venation upper surface: 147A. Venation lower surface: 147B. Petiole: Length: About 1.6 cm. Diameter: About 3 mm. Color: Upper and lower, 147B; margins, 147A.

Inflorescence description:

*Appearance.*—Daisy spray-type inflorescence form with elongated oblong-shaped ray florets. Inflorescences borne on terminals, arising from leaf axils. Disc and ray florets arranged acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 53 days later; uniform flowering habit.

*Postproduction longevity.*—In an interior environment, flowering stems will maintain good color and substance for more than two weeks in an interior environment.

*Quantity of inflorescences.*—About 8 inflorescences per flowering stem.

*Inflorescence size.*—Diameter: About 6.8 cm. Depth (height): About 1.6 cm. Diameter of disc: About 1.9 cm. Diameter of receptacle: About 1 cm.

*Ray florets.*—Shape: Elongated oblong. Length: About 3.1 cm. Width: About 1 cm. Apex: Emarginate. Base: Attenuate; short corolla tube. Margin: Entire. Texture: Smooth, satiny, glabrous; longitudinally ribbed. Aspect: Initially upright, then perpendicular to peduncle; slightly concave. Number of ray florets per inflorescence: About 28. Color: When opening: Close to 75A to 75B. Fully opened, upper surface: Close to 75B to 75C.; fading to 75D with subsequent development. Fully opened, lower surface: Close to 75C to 75D.

*Disc florets.*—Shape: Tubular. Length: About 5 mm. Width: Apex: About 1.5 mm. Base: About 1 mm. Number of disc florets per inflorescence: About 178. Color: Immature: 154A. Mature: Apex: 9A. Midsection: Close to 154D. Base: 155D.

*Peduncle.*—Aspect: Strong, angled about 40 to 45° to the stem. Length: First peduncle: About 12.2 cm. Fourth peduncle: About 19.3 cm. Texture: Pubescent. Color: 146A.

*Reproductive organs.*—Androecium: Present on disc florets only. Anther color: 12A. Pollen: Scarce. Pollen color: 12A. Gynoecium: Present on both ray and disc florets.

*Seed.*—Seed production has not been observed.

Disease resistance: Resistance to diseases common to Chrysanthemums has not been observed on plants grown under commercial conditions.

It is claimed:

1. A new and distinct cultivar of Chrysanthemum plant named 'Dark Cantata', as illustrated and described.

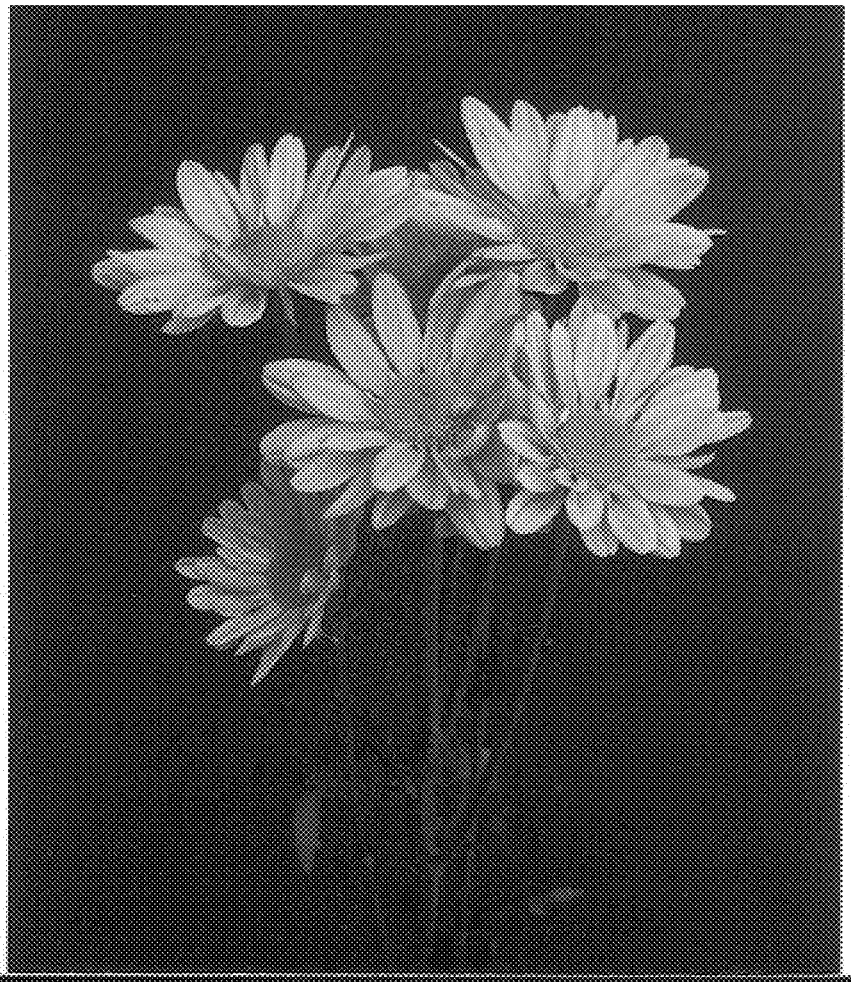
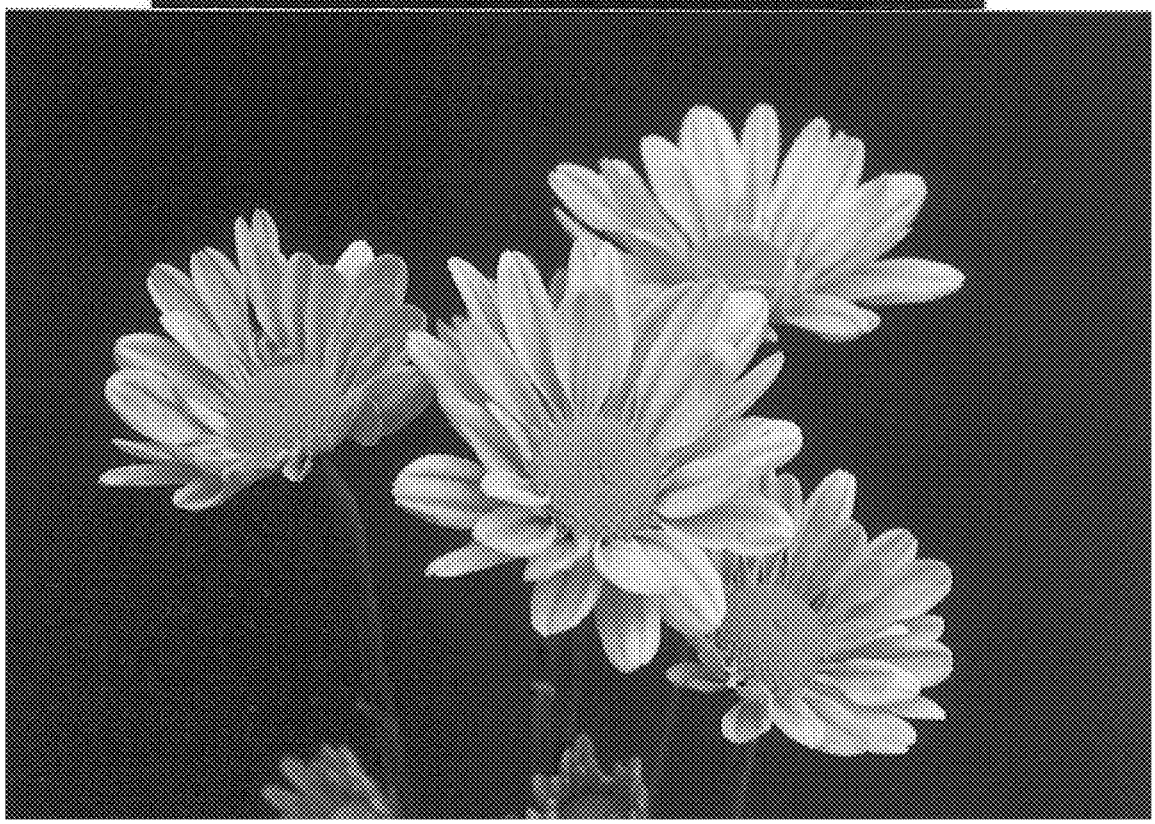

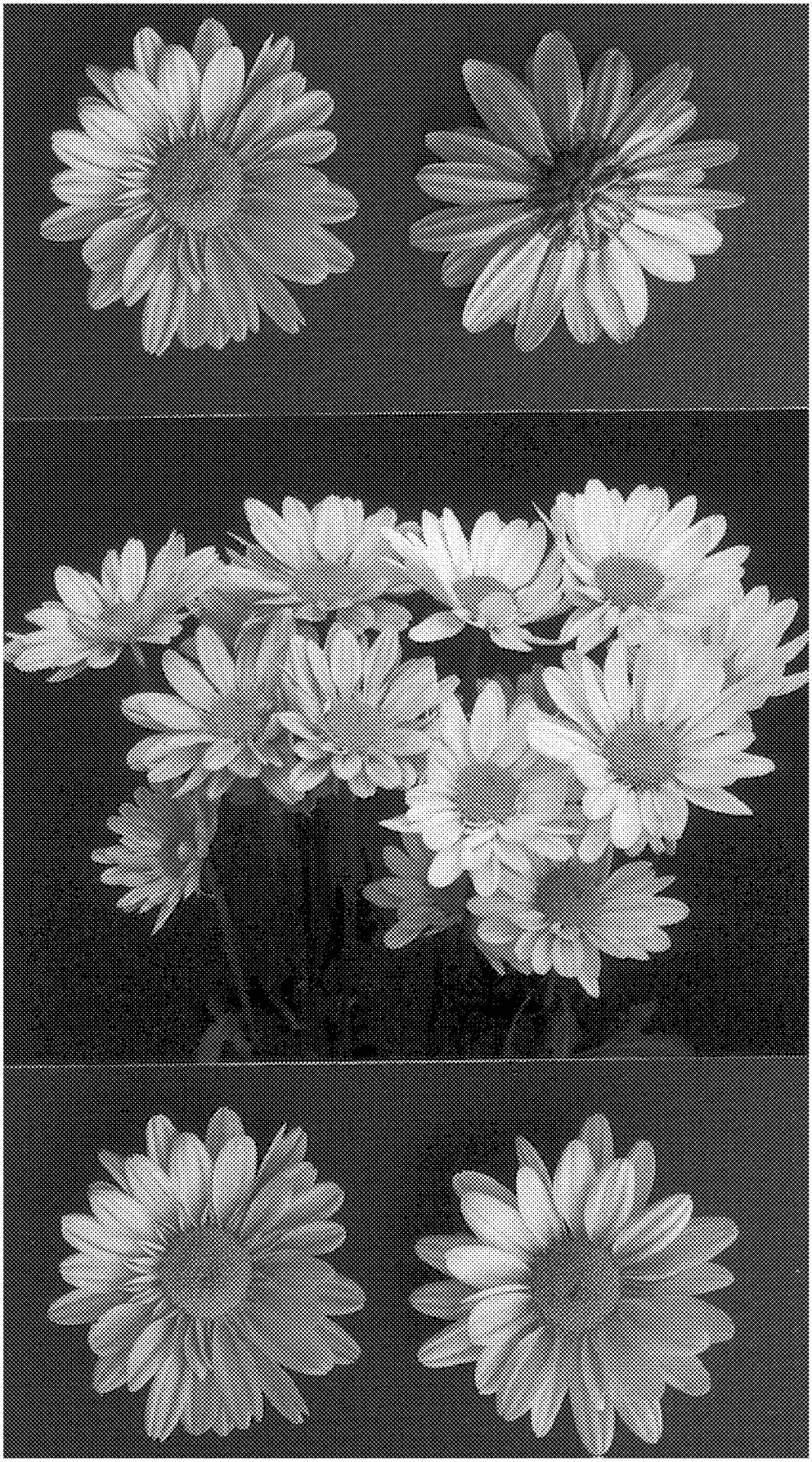

* * * * *